United States Patent [19]

Hsing

[11] Patent Number: 5,043,523

[45] Date of Patent: Aug. 27, 1991

[54] AL$_2$O$_3$ ALKENE ISOMERIZATION PROCESS AND CATALYST

[75] Inventor: Hsu-Hsiui Hsing, Sugarland, Tex.

[73] Assignee: Texas Petrochemicals Corporation, Houston, Tex.

[21] Appl. No.: 624,530

[22] Filed: Dec. 7, 1990

Related U.S. Application Data

[63] Continuation of Ser. No. 588,400, Mar. 12, 1984, abandoned, which is a continuation-in-part of Ser. No. 440,862, Nov. 12, 1982, abandoned.

[51] Int. Cl.$^5$ ............................ C07C 5/25; C07C 5/27
[52] U.S. Cl. .................................... 585/664; 585/670; 585/671
[58] Field of Search ................................ 585/664, 671

[56] References Cited

U.S. PATENT DOCUMENTS

| | | | |
|---|---|---|---|
| 2,952,719 | 9/1960 | Appell | 585/664 |
| 3,479,415 | 11/1969 | Schull | 585/664 |
| 3,558,733 | 1/1971 | Myers | 585/671 |
| 3,864,242 | 2/1975 | Brennan et al. | 585/664 |
| 3,928,485 | 12/1975 | Nagase et al. | 585/664 |
| 4,225,419 | 9/1980 | Myers | 585/671 |
| 4,229,610 | 10/1980 | Myers et al. | 585/664 |
| 4,436,949 | 3/1984 | Myers et al. | 585/664 |

FOREIGN PATENT DOCUMENTS 495050  8/1953  Canada ............................ 585/671

Primary Examiner—Jeffrey E. Russel
Attorney, Agent, or Firm—Kenneth H. Johson

[57] ABSTRACT

Gamma alumina having a sodium content of less than 0.01 weight percent sodium calculated as Na$_2$O and said alumina modified with silicon were found to be superior catalysts for the isomerization of alkenes having at least four carbon atoms, preferably with 0.01 to 1 mole of water per mole of alkene present during the isomerization. Both skeletal isomerization (e.g. n-butene to isobutene) and position isomerization (e.g. butene-2 to butene-1) are obtained.

27 Claims, No Drawings

AL$_2$O$_3$ ALKENE ISOMERIZATION PROCESS AND CATALYST

This application is a continuation of application Ser. No. 06/588,400, filed Mar. 12, 1984, now abandoned, which is a continuation-in-part of application No. 06/440,862, filed Nov. 12, 1982, abandoned.

BACKGROUND OF THE INVENTION

1. Field Of The Invention

The present invention relates to catalysts for the isomerization of alkenes, for example skeletal isomerization, such as, n-butene to isobutene, and in particular relates to gamma alumina and gamma alumina modified by treatment with a particular group of silanes to provide silicon modified gamma Al$_2$O$_3$, the method of preparing the modified catalysts, and the method of isomerization of alkenes.

2. Description Of The Related Art

It is well known that acid solids such as alumina, silica-alumina, TiO$_2$ and other metal oxides and phosphates can catalyze various reactions such as cracking, polymerization and isomerization. The degree to which each reaction will be catalyzed depends on reaction conditions and catalyst properties, such as surface acid strength, acid site concentration and site distribution, hydrophobicity, pore volume and size distribution, and surface area. Thus it is important that the surface properties of the catalyst be effectively and accurately controlled.

It has been reported in the literature that the enhancement of alumina acidity can be achieved by incorporating F and Cl through various methods.

In U.S. Pat. No. 4,038,337 the skeleton isomerization of alkenes is reported using alumina which has been reacted with a silicon compound of the general formula:

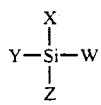

wherein X, Y, Z and W can be —R, —OR, —Cl, Br, —SiH$_3$, —COOR, —Si$_n$Cl$_m$; R being hydrogen or a hydrocarbon group of 1 to 30 carbon atoms, m and n being 1–3, preferably an ester of silicic acid, with from 0.5% to 12% by weight of silica being deposited on the alumina.

The isomerization is equilibrium limited. In the case of n-butene isomerization to isobutene, the yield in a single pass is limited by thermodynamic equilibrium to about 40 weight percent (conversion X selectivity). According to the present invention, yields of up to about 33 weight % per pass have been obtained.

It has been found now that gamma alumina can be modified to provide an active highly selective catalyst for the isomerization of n-butene to isobutene. Specifically, it has been found that a process including chemisorption of a specific group of silanes on to gamma alumina provides such a modification.

Isobutene is of significant value having diverse applications such as, for example, being one of the comonomers for butyl rubber, for use in alkylations and for dimerization to diisobutene which is an intermediate in the preparation of detergents. Butene-1 is also of significant value for polymerization to produce homopolymers and copolymers such as linear low density polyethylene.

It is an advantage of the present invention that the modified catalyst is active and highly selective for the isomerization of n-butene and isobutene. It is a further advantage of the present invention that the catalysts have long lifetimes and are easily regenerated. It is an advantage that the method of preparing the present modified catalysts provides a means of controlling the amount of silicon adsorbed on the gamma alumina. A particular feature of the present isomerization is the high conversions and selectivities obtained with both the modified and unmodified gamma alumina. A particular advantage is a very high isomerization of butene-2 to butene-1, thus n-butene feed which is not isomerized to isobutene is up graded. These and other advantages and features will become apparent from the following.

SUMMARY OF THE INVENTION

It has been discovered that alumina with a very low sodium content, i.e., less than 0.01 weight percent calculated as Na$_2$O, is a superior catalyst for use as an alkene isomerization catalyst.

The catalysts of the present invention are gamma alumina, Al$_2$O$_3$ having a sodium content of less than 0.01 wt. % as Na$_2$O and said gamma alumina modified with 0.10 to 1.50 weight % silicon preferably up to about 0.9 and more preferably about 0.15 to 0.75 weight % silicon incorporated onto the surface thereof based on total weight of catalyst.

The silicon is preferably incorporated onto the gamma alumina by a chemisorption process which comprises placing the alumina to be modified into a reactor, producing a vacuum in the reactor, flashing a liquid silane into the evacuated reactor to thereby coat said silane onto said alumina, and calcining said silane coated alumina to incorporate silicon into the alumina surface. The discovery that the silane can be deposited on the alumina by chemisorption is another aspect of the present invention.

The catalysts as described are employed in an isomerization process comprising feeding alkenes having at least four carbon atoms and preferably 4 to 12 carbon atoms, in vapor phase at a temperature in the range of 300° C. to 600° C., preferably 450° C. to 550° C. through a bed of said low sodium content gamma alumina or silicon modified gamma alumina at an LHSV (LHSV—Liquid Hourly Space Velocity in hr$^{-1}$-liquid volumes of alkene to be isomerized per volume of isomerization zone containing catalyst per hour) in the range of 0.5 to 12, preferably 1 to 8 to produce the skeletal isomer of said alkenes.

It has also been found that the presence of water in the isomerization feed improves the operation of gamma alumina in the isomerization process, i.e., an amount of water from a water saturated alkene to about 1 mole of water per mole of alkene. The presence of water in the alkene feed to the isomerization also results in an improved process of isomerization using unmodified gamma alumina.

DETAILED DESCRIPTION OF THE INVENTION AND PREFERRED EMBODIMENTS

The silanes which have been found useful for the present invention have as their general formula:

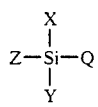

wherein X, Y and Z = —R or —OR, R = alkyl of 1 to 20 carbon atoms;

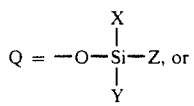

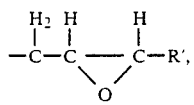

and R' = hydrogen or alkyl of 1 to 20 carbon atoms. Alkyl groups include methyl, ethyl, isopropyl, n-propyl, n-butyl, isobutyl, pentyl, hexyl, heptyl, octyl and the like. The disilanes form a particularly useful group, may be characterized by the general formula:

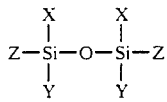

wherein X, Y and Z have the significance previously shown.

Some specific compositions which have produced excellent catalysts are compounds of the structure:

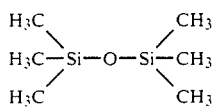

di(trimethyl silane)oxide, and

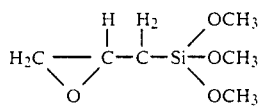

1-trimethoxy silane-2,3-epoxy propane

Gamma alumina is employed because of its desired high surface area, generally in the range of 100–350 m$^2$/gram preferably the gamma alumina has a surface area of greater than 150 m$^2$/gram up to about 300 m$^2$/gram.

The majority of modified catalysts evaluated have been prepared by a chemisorption of the silane onto the gamma alumina. It has been found that the level of sodium impurity in the gamma alumina is an important consideration. Sodium, measured as Na$_2$O is less than 0.01 wt. % to provide suitable catalysts for the isomerization of alkenes.

The alumina is normally in granular form of 12 to 20 standard U.S. mesh. Other shapes and sizes may be used, depending on the process to be utilized.

Chemisorption is a procedure which entails contacting a substrate with the material to be adsorbed thereon in an evacuated environment under conditions wherein the sorption material is vaporized and occupies the open space surrounding the substrate. Surprisingly it has been found that this approach can be used to obtain silanes coated onto alumina in the very small quantities found to modify the alumina to produce improved isomerization catalysts.

Generally the chemisorption procedure used to produce the present modified catalysts consisted of the following steps:

1. The alumina is dehydrated to remove water. This may be achieved by pumping a stream of dry gas, for example, air, across the alumina for eight hours at 300° C. Other gases such as nitrogen may be used with the temperature and duration of pumping being adjusted to desorb the water from the alumina.

2. The alumina is cooled to the temperature to be used for chemisorption, e.g., room temperature (20°–25° C.) in a vacuum.

3. The designated silane liquid to be used for chemisorption is degassed by freezing and thawing to drive out the dissolved gases.

4. The degassed silane is placed in a container attached via a control valve to the vacuum chamber containing the dried gamma alumina.

5. By opening the valve the liquid silane is vaporized into the vacuum chamber (room temperature was sufficient for the silanes evaluated, however, some silanes may be required to be at a somewhat higher temperature to volatilize into the vacuum chamber, which is a matter to be determined for each silane). The vaporized silane is adsorbed onto the alumina (generally at room temperature). The adsorption is very rapid, since the silane fills the entire chamber and is not diluted by the presence of other gases. The vaporized silane may contact the alumina for 5 seconds to 15 minutes, preferably about 5 seconds to 1 minute of time is allowed for the silane vapor to contact the alumina. It has been found that the use of high temperature, not required for volatilizing the silane, e.g., 25° C. to 500° C. produces very active catalysts.

6. The vacuum chamber is then flushed with nitrogen gas (or any other inert gas) generally at room temperature to desorb any physically adsorbed silane. It is believed that the mechanism by which the present novel and useful silicon modified gamma alumina is obtained involves the chemical reaction of the silane with specific active sites on the alumina, however, the proposed mechanism is not intended as a limitation on the invention.

7. After the flushing, the gamma alumina, containing silane adsorbed thereon, is calcined in air or an inert atmosphere at temperatures 300° C. to 700° C. preferably up to about 600° C. for 1 to 16 hours to decompose the silane. The length of the calcination did not appear to affect the results. The calcination may be carried out in a static or moving atmosphere.

The chemisorption level of silane is controlled by the valve opening between the silane liquid and the vacuum chamber and by the duration of the contact of the vaporized silane with the gamma alumina. The specific equipment used would need to be calibrated for a specific silane to obtain reproducible results.

Although room temperature is preferred for ease of operation for the chemisorption other temperatures can be used, which in conjunction with the valve opening and contact time can be used to control the dispersion of the silane on the alumina surface. Excellent catalysts have been produced at chemisorption temperatures up to 500° C., however, room temperature procedures have produced substantially equivalent catalysts.

The present catalysts may also be prepared by impregnation of the silane onto the gamma alumina catalyst. In this method the solid dried alumina is contacted with the silane in a slurry. Again, room temperature (20°-25° C.) is adequate with the amount of silane adsorbed being controlled by contact time and temperature. After the contact the alumina is flushed and calcined as described above.

The catalysts produced as described are surprisingly stable, and have, it is believed, silicon in some form incorporated into the surface. In use the catalysts tend, as with all catalysts, to exhibit a reduction in activity, possibly due to a buildup of coke. The modification of gamma alumina as described here appears to increase the surface area activity of the alumina, and also stabilizes the catalyst properties. This is especially advantageous in the need to regenerate the catalyst by burning off the coke. Generally, regeneration is desirable every twenty-four hours. Various catalysts prepared and utilized according to the present invention have been on stream in the isomerization/regeneration cycle for over two months with no sign of catalyst deactivation.

Attempts were made to extend the benefit of improved stability to alumina silica catalysts. A very active cracking silica (25% $SiO_2$) alumina was treated according to present invention to improve its isomerization properties, however, no improvement was made in that regard. Similarly, low $SiO_2$ silicated alumina treated according to the present invention did not improve catalyst activity for isomerization.

Analysis of catalysts produced according to the present invention for silicon levels (analyzed as $SiO_2$) did not establish a definite relationship between silicon level and isomerization activity, although there is a trend of increased activity with lower silicon levels within the ranges recited above.

The present silicon modified catalysts appear quite specific for skeletal isomerizations of alkenes and the presence of dienes such as butadiene in a $C_4$ feed results in rapid coking of the catalyst and loss of activity. Hence, the feed to the isomerization should contain as little diene as possible, preferably less than 0.05 mole %. It has also been found that the complete absence of water from the feed to the isomerization results in more rapid deactivation of the catalyst. Thus, in the preferred operation of this process, water is present. This has been obtained by passing the gaseous reactants through a water bath to provide a vaporous stream which was saturated with water (approximately 0.03 mole of water per mole of n-butene) under the conditions of temperature and pressure present. Water may also be added, e.g., as steam, in amounts of up to one mole of water per mole of alkene. Thus, from about 0.01 to 1.0 mole, preferably about 0.02 mole to 0.5 mole of water per alkene, e.g., n-butene, is present during the isomerization. The presence of these amounts of water also greatly improves the functioning of unmodified alumina of the type described and silicon modified alumina according to the present invention by increasing both conversion and selectivity to the isomerized product.

It has been observed that as the catalyst is deactivated with a loss in total activity, however, the drop in activity is due solely to a drop in conversion, whereas selectivity increases.

The feed to the isomerization may be substantially pure alkene, however, it is more likely that the feed will be a refinery cut, generally containing both alkenes and alkanes of the same chain length and some materials, both higher and lower boiling. The alkanes are substantially inert in the isomerization and serve as diluents. The process is carried out in vapor phase, and in addition to the hydrocarbons present, diluent gases such as nitrogen may be present.

The isomerization is carried out by feeding the alkene containing stream (preferably the stream is free of organic compounds other than hydrocarbons), in vapor phase to a reactor containing the unmodified gamma alumina or silicon modified catalysts of the present invention at temperatures in the range of 300° C. to 600° C. and LHSV of 0.5 to 12, preferably about 450° C. to 550° C. and LHSV about 1 to 8, higher temperatures being preferred for higher LHSV.

The feed to the isomerization will preferably contain only one skeletal isomer, i.e., a normal alkene or isoalkene. Although the skeletal isomer of the alkene (or isoalkene) may be present, it will be present in less than an equilibrium amount otherwise, even though the isomerization occurs the product will be substantially the same as the feed.

Generally during use of the present catalyst, conversion dropped from 43% to 30% while selectivity improved from 83% to 89% with more than 30 hours of continuous running, the result of carbon deposition. The catalyst regeneration parameters studied were temperature, length of time, regeneration feed composition, moisture and moisture level. Briefly, it was found that a regeneration sufficient for 24 hours of continuous running of the isomerization was obtained by feeding a stream of oxygen containing gas (e.g. air) at a temperature of 550° C. to 600° C. for 1 to 3 hours, e.g., one hour at 575° C., depending on the degree of coking. Higher oxygen content and flow rates shortened the regeneration period. The use of small amounts of water in the regeneration has been found to be beneficial. The water tends to reduce the temperature increase in the catalyst bed during the regeneration. The dilution of the regenerative air with an inert, e.g., nitrogen, reduces the temperature rise in the bed. Several methods of regeneration were evaluated and the one best suited for a particular operation should be selected.

The isomerization of $C_4$ (either isobutene to n-butenes or the isomerization of n-butene to isobutene) produces substantial amounts of butene-1 as an isomerization product. Specifically, butene-2 is isomerized in the present process to produce isobutene and butene-1 both in good yields. The isomerization of isobutene will similarly favor butene-1 as the isomerization product. However, in order to obtain the isomerization of butene-2 (cis and trans) to butene-1, the butene-2 in the feed is present in an amount greater than its equilibrium mixture with butene-1, otherwise, the isomerization product will contain, in addition to isobutene, butene-2 and butene-1 in the same ratio (or less desirable ratio of butene-2: butene-1) as the feed. When butene-2 is present in an amount greater than its equilibrium mixture with butene-1, the product stream will contain a greater amount of butene-1 than the feed stream.

In a preferred embodiment the isomerization feed contains an amount of n-butene in an amount greater than its equilibrium mixture with isobutene and butene-2 is present in an amount greater than its equilibrium mixture with butene-1 whereby the isomerization product stream contains a greater amount of isobutene and butene-1 than said feed stream, i.e., the coproduction of butene-1 and isobutene. In a more preferred embodiment the feed to the isomerization contains a predominate amount of butene-2 preferably greater than 60 mole % and more preferably greater than 75 mole % of butene-2. The greater the amount of butene-2 present in the feed, the greater the amount of the more desirable butene-1 isomer product in the product stream. A feed stream containing 90 mole % or more of butene-2 is especially preferred.

The following examples are intended to illustrate the invention and various permutations thereof and not to limit the scope thereof.

EXAMPLES 1-27

The alumina to be coated is placed in a 100 cc bomb connected to a vacuum pump through a valved line. The silane was in a 50 ml bomb also connected through a valved line to the vacuum pump and the silane bomb was connected through a valved line to the alumina bomb. The bombs were equipped with electric mantels for heating.

These catalysts were all prepared by chemisorption. In the general procedure the following steps were involved:
1. Alumina is pumped at 300° C. for 8 hrs. to desorb the water.
2. Cool to room temperature in vacuum.
3. Silane liquid sample is outgassed by freeze and thaw to drive the dissolved gas out of the liquid placed in the bomb and brought to the desired temperature.
4. The liquid sample valve is opened and silane vaporized into the alumina bomb and adsorbed onto the alumina surface at room temperature (or as otherwise indicated).
5. The sample from Step 4 is flushed with $N_2$ or pumped for 1-30 minutes to desorb the physically adsorbed silane molecules.
6. The silane coated gamma alumina is calcined at high temperature (as indicated) to decompose the chemisorbed silane.

In Table 1 the specifics of each catalyst preparation within the general outline are given. The Na content in TABLE I is reported as $Na_2O$.

ISOMERIZATION

The isomerizations were carried out in a fixed reactor constructed of 316 stainless steel tubing with a ½" O.D. and a ⅜" I.D. An ⅛" thermowell is located in the middle of the reactor. The reactor temperature is controlled by a two zone furnace. The first zone of 4 inches is a preheater. The second zone of 8 inches is the reactor section. The catalyst volume for each run was 10 ml of 12-20 mesh particle size. The catalyst bed length was 5 inches (with no inerts) to provide a bed length to diameter ratio over 8.0. The catalysts were tested under flow conditions of 500° C., LHSV=1.35, Flow rate n-$C_4=/N_2$ of 60/60 ml/min. and atmospheric pressure. The feed had the following composition:

| Component | Mole % |
|---|---|
| n-butane | 15 |
| n-butene-1 | |
| trans n-butene-2 | 85 |
| cis n-butene-2 | |

The results of each run are reported on the average of 24 hours on stream, except for the poorer results, which are not usually continued. The 24 hour average is after several regenerations. The product analysis was by gas chromatography. Small amounts, less than 25 mole % of $C_3$ and $C_5$ were detected in the product. Some cracking products, $CH_4$ 0.3 mole % and $H_2$, 0.3 to 0.6 mole % were detected. The conversion, selectivity (n-butenes to isobutene) and yield (C×S) are reported for each run in TABLE II.

The catalyst of Example 26 is an active cracking catalyst and continued to exhibit that property after treatment according to the present invention.

EXAMPLE 28

A catalyst according to the present invention was prepared by contacting the alumina of example 1 with di(trimethyl silane) oxide in a liquid phase slurry by the steps of heating alumina at 500° C. for 1 hr., then cooling to room temperature, adding silane slowly to the alumina with stirring until saturation, and dried in oven (110° C.) for 4 hrs.

The recovered pre-catalyst was calcined at 500° C. for 16 hours. The silicon level was 1.31 wt. %. This catalyst was placed in the reactor described and evaluated as those in Examples 1-27. The conversion of n-butene was 38 mole % with a selectivity of isobutene of 82 mole %.

EXAMPLE 29

Several methods for regenerating the present catalyst to remove coke were developed.

Method A (1) Flushed with $N_2$ at 500° C. for 30 minutes.
(2) Air/$N_2$ (3% $O_2$ in the feed) at 575° C. for one hour.
(3) Flushed with $N_2$ at 500° C. (bubbling through $H_2O$) for 45 minutes.

After more than ten cycles using this method, the catalyst of Example 3 was still completely regenerated and showed no sign of deactivation.

Method B (1) Flushed with $N_2$ at 500° C. for 30 minutes.
(2) Air at 575° C. for 1 hour.
(3) Flushed with $N_2$ at 500° C. (bubbling through $H_2O$) for 45 minutes.

Method C (1) Flushed with $N_2$ at 500° C. for 30 minutes.
(2) Air/steam (1:1) at 575° C. for 1 hour.
(3) Flushed with $N_2$ at 500° C. (bubbling through $H_2O$) for 45 minutes.

Method D (1) Flushed with $H_2O$ at 500° C. for 30 minutes.
(2) Air/steam (1:1) at 575° C. for 1 hour.
(3) Flushed with $H_2O$ at 500° C. for 30 minutes.

A comparison of each of the methods is set out in Table III. The modified catalyst of Example 3 was used for each evaluation.

EXAMPLE 30

The catalyst of Example 6 was employed in the isomerization under different conditions including the introduction of water into the feed to the reactor. The presence of water is shown to be beneficial. The conditions of operation and the results are set out in TABLE IV.

EXAMPLE 31

This example demonstrates the improvement in the skeletal isomerization of alkenes for unmodified alumina when water is added to the feed. The alumina employed was Harshaw Al-3438 in the prior examples. The alumina was unmodified. A feed of the type employed in the prior examples was employed and water added to the feed as stream at two levels 0.1 ml and 0.2 ml (liquid) per minute. The conditions and results are shown in TABLE V. The same apparatus as previously described was used. The temperature was 500° C. and LHSV was 2.94. The mole ratio of water/n-$C_4$ run B was 0.08/1 and for run C, 0.17/1.

EXAMPLE 32

This example illustrates the excellent results achieved in an isomerization using unmodified alumina having a sodium content of less than 0.01% (measured as $Na_2O$) when water is present as part of the feed to the isomerization. The LHSV was high (4.2). Conversions were high with excellent selectivity. The data is reported in TABLE VI.

EXAMPLE 33

This example illustrates the effect of the sodium content of the catalyst on the isomerization. The data is reported in TABLE VII.

EXAMPLE 34

A 1/32" extrudate, prepared by Harshaw, of alumina having a sodium content of <0.01 wt. % Na or $Na_2O$ was loaded into a 1" ID reactor (140 cc of catalyst). The feed was 1.5% n-butane and 98.5% n-butenes. The pressure drop at LHSV 4.2 was about 0.3 psig. There was little variation in pressure drop with time on stream indicating plugging of the bed was not a problem. There was a catalyst induction period of 2-3 reaction cycles (average 20 hours each cycle). The temperature of the isomerizations was around 495° C.

The favorable isomerization of butene-2 to butene-1, in addition to the skeletal isomerization to isobutene, is shown in TABLE VIII where the specific conditions and analysis for the samples are set forth.

TABLE I

| EXAMPLE | ALUMINA | SURFACE AREA Sq. M/g | Na CONTENT Wt. % | SILANE[1] | ALUMINA DESORPTION TEMP. °C. | HRS. |
|---|---|---|---|---|---|---|
| 1 | Harshaw Al-3438 | 202 | <0.01 | A | — | — |
| 2 | Harshaw Al-3438 | 202 | <0.01 | A | 300 | 8 |
| 3 | Harshaw Al-3438 | 202 | <0.01 | A | 300 | 8 |
| 4 | Harshaw Al-3438 | 202 | <0.01 | B | 300 | 8 |
| 5 | Harshaw Al-3438 | 202 | <0.01 | A | 300 | 8 |
| 6 | Harshaw Al-3438 | 202 | <0.01 | A | 300 | 8 |
| 7 | Harshaw Al-3438 | 202 | <0.01 | A | 300 | 8 |
| 8 | Harshaw Al-3438 | 202 | <0.01 | A | 300 | 8 |
| 9 | Harshaw Al-3438 | 202 | <0.01 | A | 300 | 8 |
| 10 | Harshaw Al-3438 | 202 | <0.01 | A | 300 | 8 |
| 11 | Harshaw Al-3438 | 202 | <0.01 | A | 300 | 8 |
| 12 | Harshaw Al-3438 | 202 | <0.01 | A | 300 | 8 |
| 13 | Harshaw Al-3438 | 202 | <0.01 | A | 300 | 8 |
| 14 | Harshaw Al-3438 | 202 | <0.01 | A | 300 | 8 |
| 15 | Harshaw Al-3438 | 202 | <0.01 | A | 300 | 8 |
| 16 | Harshaw Al-3438 | 202 | <0.01 | A | 300 | 8 |
| 17 | Harshaw Al-3438 | 202 | <0.01 | A | 300 | 8 |
| 18 | Harshaw Al-3438 | 202 | <0.01 | A | 300 | 8 |
| 19 | Harshaw Al-4028 | 246 | 0.02 | A | 300 | 8 |
| 20 | Harshaw Al-1602, 6% Si dioxide | 239 | 0.09 | B | 300 | 8 |
| 21 | Harshaw Al-1602, 6% Si dioxide | 239 | 0.09 | A | 300 | 8 |
| 22 | Davidson SM7-6134 | 109 | 0.035 | A | 300 | 8 |
| 23 | Davidson SM7-6169-5 | 253 | 0.035 | A | 300 | 8 |
| 24 | Kalalco Alumina, 2.5% Si dioxide | 325 | >0.01 | A | 300 | 8 |
| 25 | Kalalco | 300 | >0.01 | A | 300 | 8 |

TABLE I-continued

| | | CHEMI-SORB TEMP. °C. | SILANE ALUMINA CONTACT MIN. | REACTOR FLUSH | CALCINATION[2] TEMP. °C. | HRS. | SILICON LEVEL WT. % |
|---|---|---|---|---|---|---|---|
| 26 | Alumina, 4% Si dioxide Kalalco | 300 | >0.01 | A | 300 | | 8 |
| 27 | Alumina, 25% Si dioxide Nalco Alumina Coated w/ Si dioxide | 150 | (3) | A | 300 | | 8 |

| EXAMPLE | CHEMI-SORB TEMP. °C. | SILANE ALUMINA CONTACT MIN. | REACTOR FLUSH | CALCINATION[2] TEMP. °C. | HRS. | SILICON LEVEL WT. % |
|---|---|---|---|---|---|---|
| 1 | — | — | — | — | — | 0 |
| 2 | 25 | 15 | Pump | 300 | 1 | 0.99 |
| 3 | 25 | 0.5 | Pump | 500 | 2 | 0.62 |
| 4 | 25 | 15 | N | 500 | 2 | [3] |
| 5 | 300 | 1 | Pump | 500 | 2 | [3] |
| 6 | 25 | 15 | Pump (30 min) | 500 | 1 | 1.59 |
| 7 | 25 | 1 | Pump | 500 | 2 | [3] |
| 8 | 500 | 1 | Pump | 500 | 2 | 0.29 |
| 9 | 25 | 0.5 | Pump | 575 | 16 | [3] |
| 10 | 300 | 2 | Pump | 300 | 2 | [3] |
| 11 | 25 | 17 sec. | Pump | 500 | 12 | 0.16 |
| 12 | 25 | 27 sec. | Pump | 500 | 1 | 0.16 |
| 13 | 25 | 10 sec. | Pump | 500 | 2 | 0.16 |
| 14 | 25 | 15 sec. | N | 500 | 2 | [3] |
| 15 | 25 | 35 sec. | N | 500 | 2 | [3] |
| 16 | 64 | 5 | N | 500 | 2 | 0.79 |
| 17 | 25 | 0.5 | — | 500 | 5 | [3] |
| 18 | 25 | 5 sec. | Pump | 575 | 5 | [3] |
| 19 | 25 | 0.5 | Pump | 500 | 2 | [3] |
| 20 | 25 | 15 | N | 500 | 2 | High |
| 21 | 25 | 15 | — | 300 | 2 | [3] |
| 22 | 25 | 15 | N | 500 | 2 | High |
| 23 | 25 | 15 | — | 300 | 1 | [3] |
| 24 | 25 | 15 | N | 500 | 2 | [3] |
| 25 | 25 | 15 | N | 500 | 2 | [3] |
| 26 | 25 | 15 | — | 300 | 1 | [3] |
| 27 | 25 | 15 | N | 500 | 2 | [3] |

[1]Silanes: A = di(trimethyl silane) oxide
B = 1-trimethoxy silane-2,3-epoxy propane
[2]in air
[3]not recorded

TABLE II

| EXAMPLE | CONVERSION | SELECTIVITY | YIELD |
|---|---|---|---|
| 1 | 35 | 87 | 30.45 |
| 2 | 33 | 87 | 28.71 |
| 3 | 37 | 89 | 32.93 |
| 4 | 40 | 80 | 32.00 |
| 5 | 40 | 80 | 32.00 |
| 6 | 32 | 87 | 27.84 |
| 7 | 37 | 88 | 32.56 |
| 8 | 42 | 80 | 36.60 |
| 9 | 37 | 87 | 32.19 |
| 10 | 36 | 85 | 30.60 |
| 11 | 38 | 82 | 31.16 |
| 12 | 38 | 82 | 31.16 |
| 13 | 39 | 81 | 31.59 |
| 14 | 38 | 83 | 31.54 |
| 15 | 35 | 85 | 29.75 |
| 16 | 35 | 88 | 30.80 |
| 17 | 37 | 85 | 31.45 |
| 18 | 38 | 85 | 32.30 |
| 19 | 20 | 80 | 16.00 |
| 20 | 18 | 65 | 11.70 |
| 21 | 27 | 76 | 20.52 |
| 22 | No Activity | No Activity | |
| 23 | 25 | 80 | 20.00 |
| 24 | No Activity | No Activity | |
| 25 | Very Low Activity | Very Low Activity | |
| 26* | Very Active | Low Selectivity | |
| 27* | No Activity | No Activity | |

TABLE III

| | A | B | C | D |
|---|---|---|---|---|
| Bed Temperature Increase | Moderate | High | Low | Low |
| Regeneration Effectiveness | Good | Good | Good | Good |
| Initial Catalyst* Activity | High | High | High | Somewhat Lower |
| Initial Catalyst* Selectity | Somewhat Lower | Somewhat Lower | Somewhat Lower | High |

*on start up following each regeneration

TABLE IV

| Catalyst Sample | LHSV | Flow Rate n-butene/N ml/min. | Feed Passed Through Water | Time on Stream Hrs. | Conversion mole % | Selectivity mole % |
|---|---|---|---|---|---|---|
| Ex. 6 | 1.35 | 60/60 | NO | — | 32 | 87 |
| Ex. 6A | 1.35 | 60/60 | YES | 22.2 | 37 | 88 |

TABLE IV-continued

| Catalyst Sample | LHSV | Flow Rate n-butene/N ml/min. | Feed Passed Through Water | Time on Stream Hrs. | Conversion mole % | Selectivity mole % |
|---|---|---|---|---|---|---|
| Ex. 6B | 2.70 | 120/120 | NO | 23 | 17 | 97 |
| Ex. 6C | 2.70 | 120/120 | YES | 23.7 | 27 | 90 |

TABLE V

| RUN | FLOW RATE, n-butene | ml/min. Water-liq | ON STREAM Hrs | CONV. mole % | SEL. mole % |
|---|---|---|---|---|---|
| A | 1600 | 0.0 | 42.7 | 15 | 86 |
| B | 1600 | 0.1 | 44.5 | 24 | 88 |
| C | 1600 | 0.2 | 41.1 | 25 | 89 |

TABLE VI

Catalyst: Al-3438 of Harshaw (alumina, low sodium level, <0.01%)
Conditions: LHSV = 4.2
Temp, °C. = 515
Water (ml/min.) = 0.4
Feed Composition: 84% n-Butenes, 16% n-Butane Test Results:

| Time on stream Hours | Conv. mole % | Select. mole % |
|---|---|---|
| .2 | 39 | 86 |
| 2.3 | 35 | 87 |
| 18.6 | 30 | 88 |
| 21.6 | 28 | 88 |

TABLE VII

Catalyst: Al-4028 of Harshaw (alumina, sodium level, 0.02%)
Conditions: LHSV = 1.35
Temp, °C. = 500
Bubbled through water
n-Butene/nitrogen = 1.0
Feed Composition: 84% n-Butenes, 16% n-Butane Test Results:

| Time on stream Hours | Conv. mole % | Select. mole % |
|---|---|---|
| .1 | 10 | 89 |
| 2.5 | 5.8 | 92 |
| 20.1 | 5.3 | 93 |

TABLE VIII

TEST CONDITIONS:
Temperature - 493 C.
LHSV - 4.2
H2O (Mole %) - 20.0
Feed Compositions - 2.9% n-Butane, 1.25% Butene-1, 95.85% Butene-2
TEST RESULTS:

| HOURS ON STREAM | PRODUCT DISTRIBUTION (Mole %) | | | | | |
|---|---|---|---|---|---|---|
| | BUTENE-2 (t) | BUTENE-2 (c) | BUTENE-1 | ISOBUTENE | N-BUTANE | BALANCE |
| 1.25 | 25.66 | 18.73 | 17.43 | 29.86 | 2.96 | 5.45 |
| 18.45 | 28.23 | 20.00 | 19.64 | 25.39 | 3.10 | 3.64 |

The invention claimed is:

1. A process for the isomerization of alkenes comprising feeding a stream in vapor phase containing $C_4$ alkenes and from about 0.01 to 1.0 mole of water per mole of alkene, through a fixed bed of particulate catalyst consisting of gamma alumina having a sodium content of less than 0.01 weight percent, calculated as $Na_2O$, at a temperature in the range of 300° C. to 600° C. at an LHSV in the range of 0.15 to 12.

2. The process according to claim 1 wherein the temperature is in the range of 450° C. to 550° C. and the LHSV is in the range of 1 to 8.

3. The process according to claim 1 wherein from about 0.02 to 0.5 mole of water per mole of alkene is present in said feed.

4. The process according to claim 3 wherein butene-2 is present in said feed in an amount greater than its equilibrium mixture with butene-1, said temperature is in the range of 450° C. to 500° C., the LHSV is in the range of 1 to 8 and a product stream is recovered containing a greater amount of butene-1 than said feed stream.

5. The process according to claim 1 wherein said feed contains less than 0.05 mole percent of diene.

6. The process according to claim 4 wherein n-butene is present in said feed in an amount greater than its equilibrium mixture with isobutene and a product stream is recovered containing a greater amount of isobutene and butene-1 than said feed stream.

7. The process according to claim 6 wherein butene 2 comprises a predominate amount of said feed stream.

8. The process according to claim 7 wherein butene-2 comprises greater than 60 mole % of said feed stream.

9. The process according to claim 8 wherein butene-2 comprises greater than 75 mole % of said feed stream.

10. The process according to claim 9 wherein butene-2 comprises greater than 90 mole % of said feed stream.

11. A process for producing butene-1 comprising feeding a $C_4$ alkene stream containing butene-2 in an amount greater than its equilibrium mixture with butene-1 and from about 0.01 to 1.0 mole of water per mole of alkene, in vapor phase at a temperature in the range of 300° C. to 600° C., at an LHSV in the range of 0.15 to 12, through a fixed bed of particulate catalyst consisting of gamma alumina having a sodium content of less than 0.01 weight percent, calculated as $Na_2O$.

12. The process according to claim 11 wherein the amount of isobutene present in said feed stream is less than its equilibrium mixture with n-butene.

13. The process according to claim 12 wherein butene-2 is the predominate $C_4$ alkene present in said feed stream.

14. The process according to claim 13 wherein butene-2 comprises greater than 60 mole % of said feed stream.

15. The process according to claim 14 wherein butene-2 comprises greater than 75 mole % of said feed stream.

16. The process according to claim 15 wherein butene-2 comprises greater than 90 mole % of said feed stream.

17. The process according to claim 16 wherein a product stream is recovered containing butene-1 and isobutene in an amount greater than said feed stream.

18. A process for the coproduction of butene-1 and isobutene comprising:
(a) feeding a $C_4$ alkene stream containing n-butene in an amount greater than its equilibrium mixture with isobutene and containing butene-2 in an amount greater than its equilibrium mixture with butene-1 and from about 0.01 to 1.0 mole of water per mole of alkene, in vapor phase at a temperature in the range of 300° C. to 600° C., at an LHSV in the range of 0.15 to 12, through a fixed bed of particulate catalyst consisting of gamma alumina having a sodium content of less than 0.01 weight percent, calculated as $Na_2O$.
(b) recovering a product stream containing a greater amount of butene-1 and isobutene than said feed stream.

19. The process according to claim 18 wherein butene-2 comprises greater than 60 mole % of said feed stream.

20. The process according to claim 19 wherein butene-2 comprises greater than 75 mole % of said bed stream.

21. A process for the skeletal isomerization of alkenes comprising feeding a stream in vapor phase containing alkenes having four to twelve carbon atoms and from about 0.01 to 1.0 mole of water per mole of alkene, through a fixed bed of particulate catalyst consisting of gamma alumina having a sodium content of less than 0.01 weight percent, calculated as $Na_2O$, at a temperature in the range of 300° C. to 600° C. at an LHSV in the range of 0.15 to 12.

22. The process according to claim 21 wherein the alkene has four carbon atoms.

23. The process according to claim 21 wherein the temperature is in the range of 450° C. to 550° C. and the LHSV is in the range of 1 to 8.

24. The process according to claim 21 wherein from about 0.02 to 0.5 mole of water per mole of alkene is present in said feed.

25. The process according to claim 24 wherein said alkene has four carbon atoms and n-butene is present in said feed in an amount greater than its equilibrium mixture with isobutene, said temperature is in the range of 450° C. to 500° C., the LHSV is in the range of 1 to 8 and a product stream is recovered containing a greater amount of isobutene than said feed stream.

26. The process according to claim 21 wherein said feed contains less than 0.05 mole percent of diene.

27. A process for isomerization of an n-butene-comprising feed stream, the process comprising:
(a) feeding a vaporized predominantly n-butene-comprising feed stream at an LHSV in the range of 1 to 8 into a reactor containing a fixed bed of particulate gamma alumina catalyst containing less than 0.01 weight % Na calculated as $Na_2O$ and maintained at a temperature in the range of 450°-550° C. and characterized by the substantially continuous feed of from about 0.01 to 1.0 mole of water per mole of n-butene to said reactor during said isomerization;
(b) terminating said feed of n-butenes before a substantial decline in the conversion of said n-butenes;
(c) feeding an oxygen containing gas through said fixed bed of particulate gamma alumina maintained at a temperature in the range of 550° to 600° C. for a period of time to remove coke deposited on said alumina catalyst and thereby regenerate said catalyst and
(d) repeating step (a) to (c).

* * * * *